United States Patent
Freeman et al.

(10) Patent No.: US 8,277,490 B2
(45) Date of Patent: Oct. 2, 2012

(54) TRANSLATIONAL MANIPULATION POLYAXIAL SCREW HEAD

(75) Inventors: Thomas B. Freeman, Tampa, FL (US); Wesley M. Johnson, Tampa, FL (US)

(73) Assignee: University of South Florida, Tampa, FL (US)

(*) Notice: Subject to any disclaimer, the term of this patent is extended or adjusted under 35 U.S.C. 154(b) by 197 days.

(21) Appl. No.: 12/714,953

(22) Filed: Mar. 1, 2010

(65) Prior Publication Data

US 2010/0234891 A1 Sep. 16, 2010

Related U.S. Application Data

(63) Continuation of application No. PCT/US2008/075003, filed on Sep. 2, 2008.

(60) Provisional application No. 60/969,322, filed on Aug. 31, 2007.

(51) Int. Cl.
*A61B 17/70* (2006.01)
(52) U.S. Cl. .......... 606/266; 606/267; 606/269
(58) Field of Classification Search .......... 606/266, 606/254, 264, 278, 279, 256, 261, 270, 269, 606/287, 267, 305, 306, 307, 308; 411/427
See application file for complete search history.

(56) References Cited

U.S. PATENT DOCUMENTS

| | | | |
|---|---|---|---|
| 5,520,690 A | 5/1996 | Errico et al. | |
| 5,882,350 A | 3/1999 | Ralph et al. | |
| 6,565,567 B1 * | 5/2003 | Haider | 606/266 |
| 6,626,908 B2 * | 9/2003 | Cooper et al. | 606/266 |
| 6,835,196 B2 * | 12/2004 | Biedermann et al. | 606/308 |
| 6,896,677 B1 * | 5/2005 | Lin | 606/266 |
| 7,211,086 B2 | 5/2007 | Biedermann | |
| 7,291,153 B2 | 11/2007 | Glascott | |
| 7,678,139 B2 * | 3/2010 | Garamszegi et al. | 606/328 |
| 7,722,651 B2 * | 5/2010 | Kwak et al. | 606/265 |
| 7,951,174 B2 * | 5/2011 | Kwak et al. | 606/270 |
| 2005/0187548 A1 | 8/2005 | Butler et al. | |
| 2005/0192571 A1 | 9/2005 | Abdelgany | |
| 2005/0261687 A1 | 11/2005 | Garamszegi et al. | |
| 2006/0200131 A1 | 9/2006 | Chao et al. | |
| 2006/0241600 A1 | 10/2006 | Ensign et al. | |
| 2006/0264933 A1 | 11/2006 | Baker et al. | |
| 2006/0276792 A1 | 12/2006 | Ensign et al. | |
| 2007/0161999 A1 | 7/2007 | Biedermann et al. | |

FOREIGN PATENT DOCUMENTS

WO 2007035884 A2 3/2007

* cited by examiner

*Primary Examiner* — Pedro Philogene
(74) *Attorney, Agent, or Firm* — Robert Varkonyi; Smith & Hopen, P.A.

(57) ABSTRACT

A novel surgical screw is presented as a polyaxial, multiaxial, or monoaxial screw. The polyaxial screw allows versatile angulation between a bone anchor section and a screw body and allows the surgeon to attach a rod to the invention in a top-loading manner and manipulate the rod to accommodate a patient's body and the surgical goals. The screw uses a rod saddle to seat a rod, and permits the surgeon to sagitally manipulate the rod. After implantation of the screw and insertion of the rod, a locking screw is used to fix the angle and position of the rod and screw body.

27 Claims, 4 Drawing Sheets

TRANSLATIONAL MANIPULATION POLYAXIAL SCREW HEAD

CROSS REFERENCE TO RELATED APPLICATIONS

This application is a continuation of prior filed International Application, Serial Number PCT/US2008/075003 filed Sep. 2, 2008, which claims priority to U.S. provisional patent application No. 60/969,322 filed Aug. 31, 2007 which is hereby incorporated by reference into this disclosure.

FIELD OF INVENTION

This invention relates to surgical implantable instruments. Specifically, the invention relates to osteosurgical screw devices.

BACKGROUND OF THE INVENTION

Spinal implants constitute 40% of all orthopedic implants, with pedicle screws among the most frequently implanted devices. Spinal fixation systems are used in surgery to align, adjust, and fix the spinal column, many times by fusing vertebrae together. Typical spinal fixation systems use a rod or plate to support the spine and to properly position the vertebrae. Anchors, consisting of pins, bolts, screws, and hooks are used to engage the vertebrae and support the rod or plate and are driven into the pedicles of the spine. While the rod or plate varies in size, length, and shape, the rod is generally modified before insertion into the anchor, due to the complex nature of spinal anatomy. In many instances, two or more non-aligned anchors require bending of the rod or plate, thereby introducing fatigue resistance into the rod or plate.

Currently, there are several models of screws on the market, of which there are polyaxial screws and monoaxial screws. Polyaxial screws can be locked/rigid (monoaxial) or variable angle (polyaxial) based on simple intraoperative manipulations to change the stability of the top loading (tulip) end of the screw. A new category of polyaxial screws has been developed by several companies that allow the screw to change from variable angle to rigid at the will of the surgeon. These screws, however, lack the ability to be manipulated surgically in a sagittal direction, limiting a surgeon's ability to manipulate the vertebral bodies to create sagittal alignment.

The rod attaches to the screw at the body, either using a top loading or side loading arrangement. Most conventional top-loading polyaxial screws do not address cantilever failure and fail to permit adequate flexibility because the rod or plate rests too close to the screw rotational center. Placing a rod into side-loading screw requires significant forces to insert the rod into the screw body if the screws are not perfectly aligned. As such, many side-loading systems require two surgeons to reduce the spinal rods into the screw settings prior to tightening. This can also lead to fracture of the vertebral body/pedicle by displacement of the screw, weakening of the construct or lateral rotation of the vertebral body leading to a rotational deformity which is not intended.

The TSRH SiLo 5.5 Spinal System Sagittal Adjusting Screw (SAS) was designed to combine the correction of a fixed angle screw with a multi-axial screw, reducing the stress incurred on the bone during correction maneuvers. The SiLo 5.5 Spinal System also features a device that allows surgeons to use one hand in securing rods to pedicle screws and provides greater reduction than current systems. However, once the SiLo screw is rigid, the SiLo screw also requires exact alignment for placement of the rod. It is not possible to manipulate the screw relative to the rod in a sagittal direction for manipulation of the vertebral bodies, whereas in a trauma situation, it is frequently desirable to manipulate the vertebral bodies to correct a kyphotic deformity due to a burst fracture.

The Depuy EXPEDIUM screw has an inner and outer head screws which allows sequential tightening of either the polyaxial rotational component of the head or tightening of the screw onto the rod. This allows the surgeon to either distract independently or make the screw rigid versus polyaxial on an independent basis. However, the EXPEDIUM screw cannot be manipulated in a sagittal direction in relation to the rod, which is frequently required to change sagittal malalignment or imbalance. Examples of this include trauma situations with burst fractures managed from posterior surgical approaches, as well as flat back cases where increasing sagittal lordosis may be desired, among others.

SUMMARY OF THE INVENTION

Surgical implant systems are used to strengthen, stabilize, and align anatomic structures. Spinal implant systems are designed to apply and withstand relatively high mechanical forces so as to hold the spine in alignment while fusion takes place. However, it is advantageous to reduce the implant size to provide minimal disruption to the biological environment, while still allowing quick and efficient implantation during surgery. Thus, the implant components must be easy to assemble and large enough to enable the surgeon to easily handle them.

The screws available in the art require nearly perfect technique by the surgeon to align the screws. Current screw designs eliminate the ability to take advantage of anatomic variability from patient to patient or vertebral body level to vertebral body level. Moreover, screw placement was developed to eliminate a skeletal deformity, and that deformity, by definition, creates malalignment and therefore a rigid screw would require significant reduction to insert the rod into the screw. Thus, there exists a need in the art to develop screws that may be placed in perfect alignment, yet retain the ability to reduce sagittal misalignment after the rods have been placed.

The subject of this patent is a new combined polyaxial, multiaxial, monoaxial, or rigid screw that can be manipulated intraoperatively in the sagittal direction with relation to the rod. This screw allows in either the X, Y, or Z plane alone, or rotational manipulation of the screw in any three planes, permitting correction of varying skeletal deformities, including rotational, malalignment, longitudinal angulation, compression or distraction, or bust fracture deformities. The novel screw allows less torque to be placed on the screw in order to place a rod into the screw body, which advantageously reduces screw failure during manipulation. The screw also incorporates the advantages of a polyaxial screw with sagittal reduction: namely rods can easily be placed into screws that are placed in perfect alignment, yet retain the ability to reduce sagittal misalignment after the rods have been placed.

Accordingly, the present invention provides a surgical screw allowing versatile angulation between a bone anchor section and a screw body section, thereby allowing a surgeon to manipulate the surgical screw in multiple dimensions during implantation. Further, the present invention allows the surgeon to attach a rod to the invention in a top-loading manner and manipulate the rod to accommodate a patient's body and the surgical goals.

The screw permits the screw body to pivot in relation to the bone anchor section. The screw comprises a bone anchor with a proximal head and distal shaft extending along a longitudinal shaft and configured to engage bone. The proximal head comprises a narrow neck section which expands into a convex mating section and a flattened face, substantially less curved than the remaining mating section, opposite the longitudinal shaft. Disposed in the flattened face is a tool receiving indent, such as an indent that accepts a hex driver, torx driver, Philips head screw driver, or flat head screw driver. The screw body consists of a receiver, rod saddle and compression nut. A rod locker is also envisioned in some embodiments of the invention. The proximal head is set in a concave recess within the receiver, which allows the bone anchor to pivot relative to the receiving member in some embodiments. Alternatively, the proximal head sits in the receiving member such that the bone anchor section may only rotate 360 degrees, but is incapable of pivoting in any other direction.

The bone anchor section extends distally from the head to form a screw shaft with anchor threads attached. The anchor threads may be single leads, double leads, fixed screw leads, and variable screw leads adapted for attachment to an anatomical body. In some embodiments, the bone anchor is adapted for insertion into cancellous bone, specifically the pedicle of a vertebra.

The bone anchor rests inside the receiver. In some embodiments, the recess is a semi-circular, convex recess adapted to allow full three dimensional pivoting of the bone anchor. Other embodiments provide a more angular recess, such as a cylinder shape, restricting the bone anchor movements to rotation only. An opening is disposed in the receiver to allow the screw shaft and anchor threads to extend distally from the receiver, projecting through the opening. Disposed along the longitudinal axis of the receiver wall is a plurality of U-shaped openings adapted to receive the rod.

The surgical screw optionally uses a rod locker, disposed within the receiver body and proximal to the bone anchor head. In some embodiments the rod locker uses a rounded base adjacent to the bone anchor head and adapted to allow free articulation of the bone screw. The base may be a concave shape, permitting free rotation of the head in a spherical cavity or a convex shape, allowing the head to pivot along the most distal part of the rod locker base. Alternatively, the base is a flat surface, only permitting rotation, but not angular pivoting, of the bone anchor. The rod locker has a plurality of openings disposed on the longitudinal axis of the rod locker walls, adapted to receive the rod. These openings may be spherical openings, U-shaped openings, or combined spherical-U-shaped openings, or resembling an inverted omega. A rod saddle is seated within the rod locker. The rod locker may have a curved upper surface adapted to the accept rod saddle. In embodiments of the surgical screw that do not utilize the rod locker, the rod saddle is disposed within the receiver and is proximal to the bone anchor head. In such embodiments the rod saddle acts to lock the rod in its final placement as well as lock the bone anchor head.

The rod saddle provides a seat for the rod, regardless of whether the surgical screw utilizes a rod locker. The rod saddle may be spherical, spheroid, oval, or ovoid. In some embodiments, the rod saddle is disposed below the rod, above the rod, or comprises two rod saddles, one above the rod and one below the rod. Where two rod saddles are used, the rod saddles may be identical or may be different sizes, shapes, or sizes and shapes. The rod saddle comprises two elements, a mating face adapted to accept a rod, and an articulating face. In some embodiments, the rod saddle has a concave mating surface and convex articulating surface, allowing the rod to pivot within the screw body. Importantly, the rod saddle permits a surgeon to manipulate the rod, especially in a sagittal direction. The rod saddle further includes a locking mechanism of a rough surface, a notched surface, or a knurled surface that allows the surgeon to set the rod in the surgical screw.

The screw utilizes a rod or other device to anchor the rod to a vertebra, such as a rod anchor, screw, or hook; and a device to apply compression to the rod in order to hold it in place relative to the anchor. Such a compression device includes internal compression members, such as an compression nut, step locking lug, or plug.

A compression nut screws into the surgical screw after placing the rod, locking the screw. In some embodiments, the receiver body has threading on in inner face, at the proximal end and opposite the bone anchor section. Alternatively, the rod locker has threading at the proximal end. The compression nut comprises external threading which screws into the receiver body or rod locker. Screwing the compression nut into the surgical screw compresses the components of the surgical screw, thereby locking the device. In some embodiments, the compression nut compresses the rod against the rod saddle, locking the rod saddle using the rod saddle locking mechanisms and also locking the rod. In some embodiments, the compression nut also compresses the rod locker into the receiver, locking the bone anchor section. In alternative embodiments, a step locking lug is used to tighten the surgical screw after placing the rod. The step locking lug has a plurality of lands and grooves, making a plurality of locking rings. The locking rings snap into corresponding locking rings in the surgical screw body, locking the surgical screw components. The locking rings snap into the internal face of the receiver in some embodiments.

The present invention therefore provides a polyaxial surgical screw, a multiaxial surgical screw, or a monoaxial surgical screw surgical screw of a size which can be conveniently handled by the surgical staff during surgical implantation and which can be tightened to proper tightness without requiring the use of a torque wrench.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
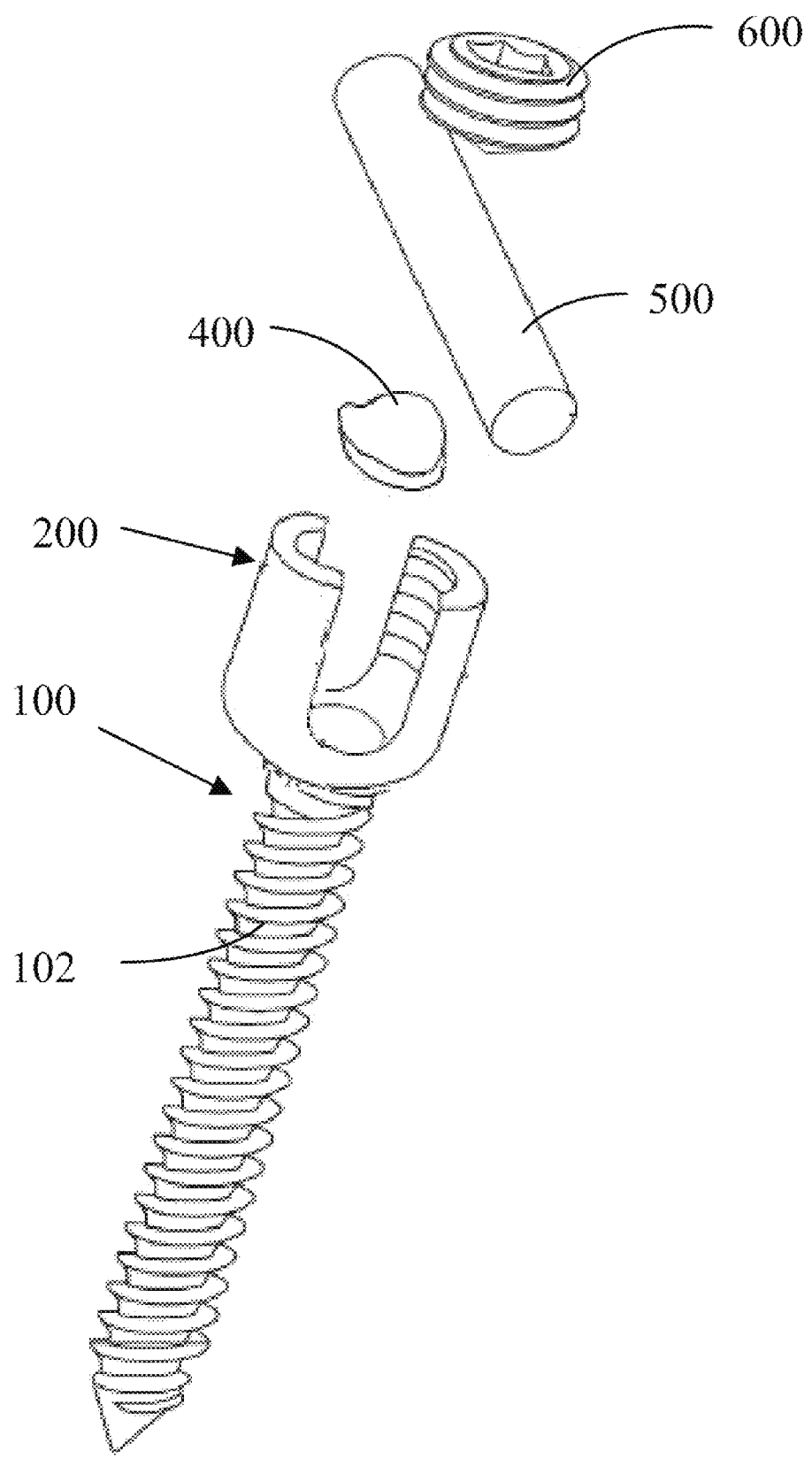
FIG. 1 is a perspective, exploded view of a bone screw of the present invention depicting a single rod saddle mated to the bottom of a rod. The bone anchor is fitted into the receiver.

"Patient" is used to describe an animal, preferably a human, to whom treatment is administered, including prophylactic treatment with the compositions of the present invention.

"Concave" is used herein to describe an indented surface without reference to the specific shape of the indented surface. As nonlimiting examples, the concave face may be tubular with a round cross section, oval cross section, square cross section, or rectangular cross section.

"Rod" is used herein to refer to a device used to connect a plurality of bone screws together as is known in the art. This includes, without limiting the definition, rods, cables, bars, and wires.

"Substantially free" is used to describe the ability of a component to articulate in multiple axis with little interference from the other components of the device. A component may substantially free to pivot if the component may articulate within a range of 60°, preferably 90°, more preferably 120°, or even more preferably 160°.

The present invention provides a bone screw assembly in a spinal fixation system utilizing the pedicle of the spine. One skilled in the art will recognize that the invention is not limited to use in spinal surgery, and that the instrument and methods described herein can be adapted for use with any suitable surgical device and may be adapted for use in selected position in a variety of medical procedures. The present invention is described below using exemplary embodiments to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein.

During spinal deformity surgeries, it is often necessary to de-rotate the vertebral bodies to normalize the spine. Because patient anatomy varies, insertion of fixed angle surgical screws, where the anchor segment is set at a fixed angle relative to the rod, can be difficult. Polyaxial and multi-axial screws, which allow the screw shank to pivot about the head portion, permit the screw to be tailored to a patient's unique anatomy before and during insertion of the rod.

The exemplary surgical screw assemblies of the inventive embodiments may be used to engage one or more spinal fixation elements to bone. For example, a surgical screw assembly may be employed to fix a spinal plate, rod, and/or cable to a vertebra of the spine. Although the exemplary surgical screw assemblies described below are designed primarily for use in spinal applications, and specifically the pedicle region of a vertebra, one skilled in the art will appreciate that the structure, features and principles of the exemplary surgical screw assemblies, as well as the other exemplary embodiments described below, may be employed to couple any type of orthopedic implant to any type of bone or tissue. The surgical screw assembly facilitates correcting the position of a patient's vertebra in which the surgical screw is implanted.

Figure 2:
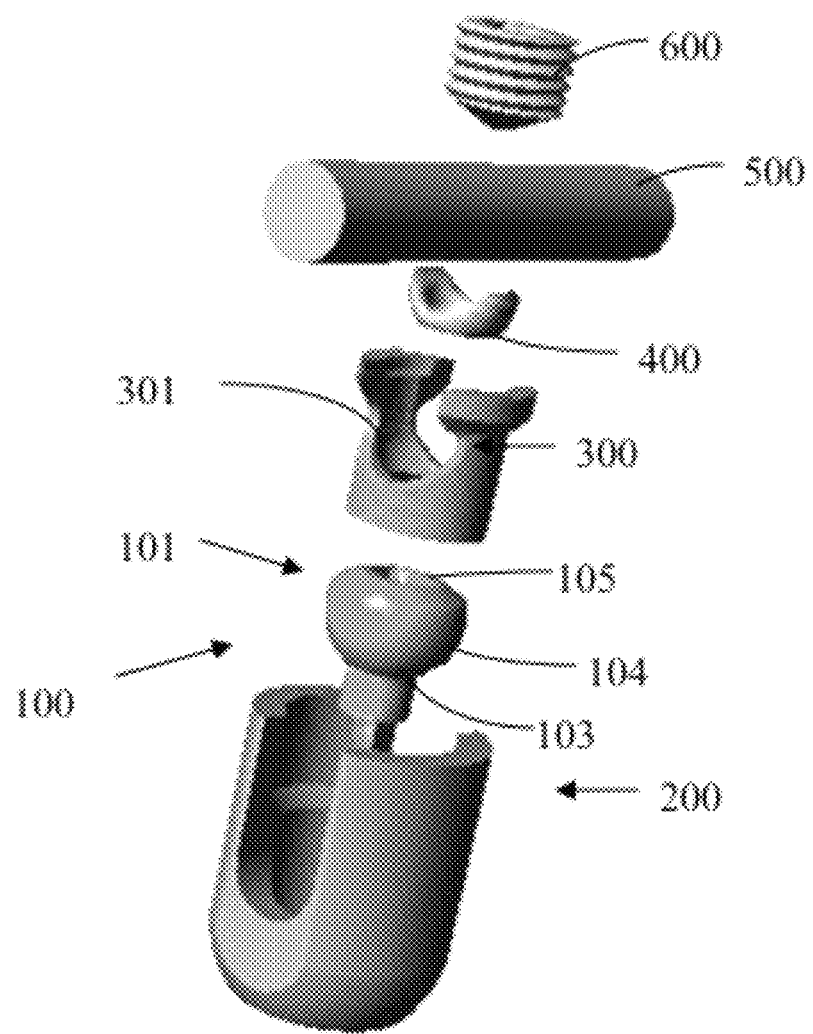
FIG. 2 is an enlarged, exploded perspective view of a surgical screw of the present invention depicting a bottom rod saddle. The bone anchor shaft and threads are not shown.

A variable angle surgical screw permitting sequential tightening of either the polyaxial rotational component of the head or tightening of the screw onto the rod is provided, as seen in FIG. 1. The variable angle screw comprises bone screw 100 with threads designed for insertion into cancellous bone, particularly the pedicle of a vertebrae. Bone screw 100 consists of a proximal head section 101 and distal bone anchor section 102, as seen in FIG. 2. Head section 101 consists of a narrow neck section 103 which expands into a convex mating section 104. Mating section 104 is semi-spherical. The proximal-most section of mating section 104 is substantially less curved than the remaining mating section 104. On the proximal face of bone screw 100, a tool receiving indent 105 is provided for accepting a hex driver, torx driver, or other tool. Anchor section 102 consists of leads known in the art, including single leads, double leads, fixed screw leads, and variable screw leads.

The bone screw head is received by tubular receiver 200 having an internal, semi-circular, convex recess and adjacent opening 201 in the distal end of receiver 200. The convex recess of receiver 200 mates with head section 101 of bone screw 100, such that bone anchor 102 projects through opening 201 in receiver 200 and bone screw 100 freely articulates in the convex recess of receiver 200. Receiver 200 has a plurality of U-shaped openings 202 disposed on the walls of receiver 200, adapted to receive rod 500 from the top of receiver 200 and opposing opening 201 (top-loading). Further, opening 201 is smaller than head section 101, such that cone anchor 100 is retained in receiver 200 without falling out of the receiver.

Rod locker 300 is a tubular component disposed within receiver 200 and is proximal to head section 101, i.e. sits atop the head of bone screw 100. Rod locker 300 is adapted to allow articulation of bone screw 100 and has a plurality of U-shaped rod openings 301 disposed on the walls of rod locker 300 and adapted to accept rod 500. In some embodiments, rod locker 300 has a unique U-shaped opening 301, comprising a spherical opening or combination of U-shaped and spherical opening. This is depicted in FIG. 2, where the sides of the opening flare out and subsequently narrow again. In some embodiments, the distal end of rod locker 300 also has a curved proximal mating face, adapted to accept rod saddle 400. The curved mating face aids in angular motion for rod 500. Rod saddle 400 is proximal to rod locker 300 and is adapted to mate rod locker 300 and rod 500. Rod saddle 400 utilizes a curved mating surface on its proximal face, which provides angular motion for rod 500. Rod saddle 400 also possesses a rounded distal face, allowing rod saddle 400 to articulate within rod locker 300. Rod 500 is disposed proximal to rod saddle 400 and is within the U-shaped openings of receiver 200 and rod openings 301. Rod 500 is used to connect adjoining vertebrae as is known in the art.

Figure 3:
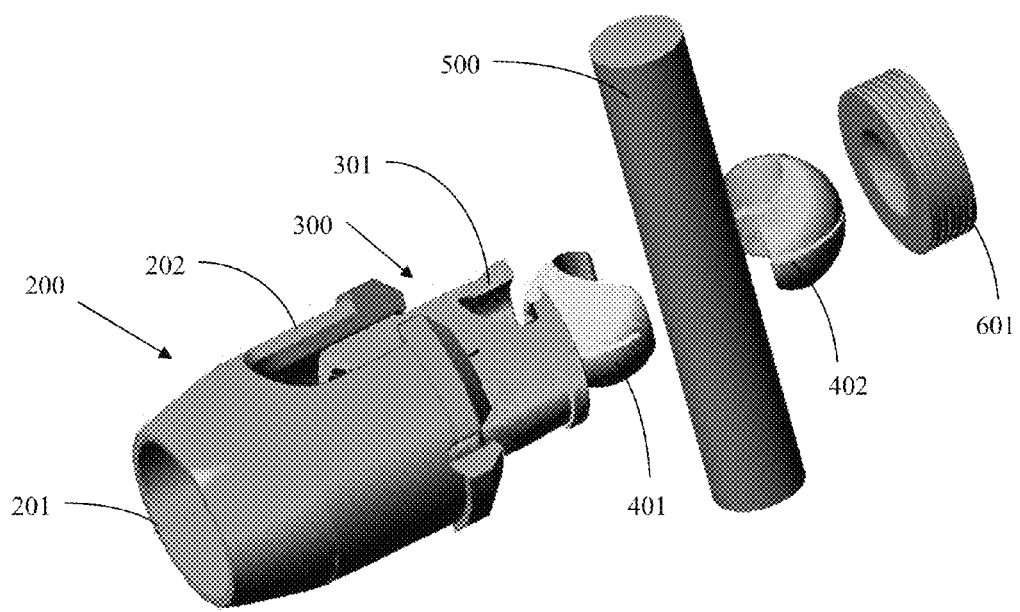
FIG. 3 is an enlarged, exploded perspective view of a surgical screw of the present invention depicting both the rod saddles above and below a rod. The bone anchor is not shown.

Alternatively, the rod saddle consists of distal rod saddle 401 and proximal rod saddle 402, seen in FIG. 3. Distal rod saddle 401 is placed atop rod locker 300 and is adapted to mate rod locker 300 and rod 500, with proximal rod saddle 402 placed atop rod 500. Distal rod saddle 401 and proximal rod saddle 402 possess curved mating surfaces, where the proximal face of distal rod saddle 401 and the distal face of proximal rod saddle 402 are adapted to accept rod 500. The distal face of distal rod saddle 401 and proximal face of proximal rod saddle 402 also possess convex, round faces, such that distal rod saddle 401 and proximal rod saddle 402 substantially form a sphere when combined. Combining distal rod saddle 401 and proximal rod saddle 402 allows free articulation of rod 500 within the U-shaped openings of receiver 200 and rod locker 300.

Figure 4:
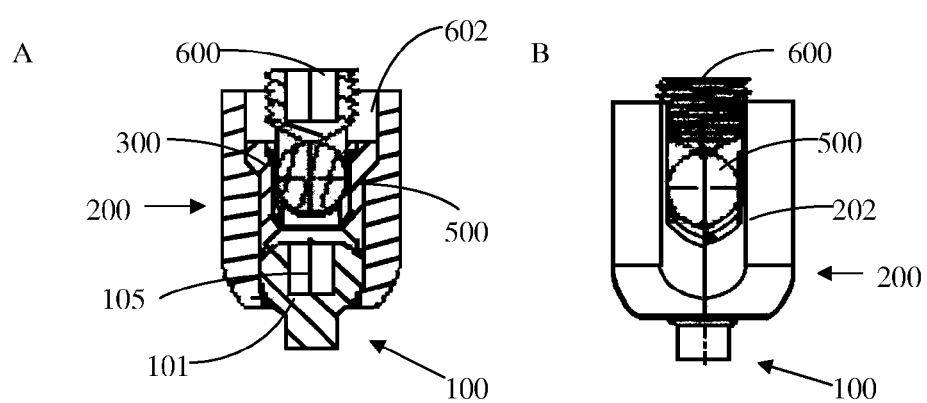
FIG. 4 is a diagram of the surgical screw in (a) a cross section view of a surgical screw of the present invention, through the center of the screw; or (b) a side view of the screw.

Compression nut 600 has at least one external thread. The at least one thread is disposed on the outside surface of the compression nut, seen in FIG. 4. The threading is adapted mate with at least one thread on the inside wall of retainer 200, such that the compression nut screws into the receiver. Screwing the compression nut into receiver 200 compresses rod 500 against rod saddle 400, thereby fixing the orientation of rod 500 in relation to receiver 200. In some embodiments, compression nut 600 also compresses rod locker 300 into receiver 200, which compresses the convex head of bone screw 100 into the receiver and locks the angular position of receiver in relation to bone screw 100. Alternatively, compression nut 600 may be step locking lug 601, seen in FIG. 3. Step locking lug 601 has a plurality of wedge or land and groove shaped rings adapted to mate with a plurality of inversely positioned wedge or land and groove shaped rings on the inner surface of receiver 200. Step locking lug 601 is designed such that when force is applied to the lug, the wedge shaped rings on step locking lug 601 slide past the wedge shaped rings on receiver 200 and step locking lug 601 snaps into receiver 200. Applying additional force causes step locking lug 601 to snap into the next wedge shaped ring, progressively tightening the surgical screw.

In some embodiments, outer set nut 602 is used to compress rod locker 300 distally into receiver 200, locking the angular position of receiver 200 in relation to bone screw 100. Outer set nut 602 is adapted to accept compression nut 600 or step locking lug 601 in the center of outer set nut 602. Outer set nut 602 may be a hollow nut with threading on the exterior and interior walls, allowing outer set nut 602 to screw into receiver 200 and permitting compression nut 600 or step locking lug 601 to screw in the center of outer set nut 602. Outer set nut 602 applies force on the rod locker, which is sufficiently large to transmit force from the outer set nut to the anchor screw head locking it, making it rigid. Independently, compression nut 600 or step locking lug 601 applies a force to the rod and then the rod saddle to the inside of the rod locker. Alternatively, outer set nut 602 and compression nut 600 or step locking lug 601 may use a plurality of inversely positioned wedge or land and groove shaped rings to snap into receiver 200, as described above.

The use of rod saddle 400 or rod saddles 401 and 402 in the polyaxial, monoaxial, or polyaxial-monoaxial surgical screw, along with the rod locker and screw head, allows the manipulation of the screw in the rigid setting (monoaxial setting). A locking mechanism is used on the articulating face of the rod saddle, which is a rough surface or a notched (knurled) surface in some embodiments. Alternatively, the rod saddle articulating face has roughness or teeth of various sizes. Where teeth are employed, the teeth lock the rod saddle in a fixed position, but allow rod motion by as the mating surface or surfaces of the rod saddle are smooth. Fully tightening the compression nut or step locking lug locks the rod into place. In some embodiments, the shape of the rod saddle is oval, or has corners on the lateral surfaces, and may be below the rod or above the rod. In certain embodiments, the rod saddle is shaped with a concave upper surface adapted to accept the rod, and a convex lower surface, adapted to mate with the rod locker and permit angular motion. This design permits the screw to allow for sagittal manipulations, especially during surgery. The design allows significant forces on the vertebral bodies to create sagittal alignment as desired by the surgeon intraoperatively, thereby allowing the surgeon rigid sagittal manipulation of vertebral bodies once the screws and rods have been placed. In addition, a similar modification is within the skill of the art and envisioned for any dual polyaxial/monoaxial screw system that uses other mechanisms for going back and forth between the dual polyaxial/monoaxial configurations.

Further, an "anti-torque" cannulated device is envisioned for use to allow for longitudinal manipulation on the surgical screw. The torque application end of the cannulated device is of sufficient thickness to allow manipulation without deformity of the anti-torque device. In addition, the cannulated device has a sufficiently close fit to the head of the polyaxial surgical screw, thereby allowing adequate manipulation without mechanical looseness. A series of holes are disposed on the sides of the anti-torque device to accommodate sagittal or longitudinal motion of the rod. Additionally, the anti-torque device is envisioned to be 14" in length, but can vary from 6-24" in length. In addition, the handle for the anti-torque device is a rounded padded handle, a "t-handle," or a folding t-handle with a rounded outer component to allow surgeon preference to be utilized.

The vertebral body or anatomic body, hereinafter the target body, of a patient is properly prepared in accordance with known and accepted surgical procedures. The surgeon drills a hole in the target body, typically using drill bits of increasing diameter, as in known in the art. After preparing a pedicle for a tap, the surgeon threads the hole in the target body using a tap, establishing threads on the walls of the hole. Typically, during the preparation of the tapped hole, the surgeon will use a probe to determine the proper angulation and depth of the hole. The surgeon repeats the above procedure for each hole required. During surgery, the surgical screw is preferably loaded into the socket of a driver, such as a hex driver or screwdriver, which would receive and grasp the screw head to avoid the head dropping into a wound. The surgical screw of the invention is inserted into the pre-drilled hole. The screw may be removed by seating a driver and reversing the direction of torque. The surgical screw is made of a sufficiently hard biocompatible material such as, for example, hardened, surgical-grade stainless steel, e.g., 22-13-5 stainless steel. Other appropriate materials such as titanium or biocompatible plastics or composites may be used with the appropriate revision to the prescribed predetermined load limit and rates of compression. The device of the present invention is preferably radiodense, permitting the surgeon to assess the position of the device in a manner known in the art.

The current surgical screw invention allows the rod to be placed into the screw while in the variable angle setting. This allows for deviation in technique, anatomy, as well as deformity when the rod is placed. Also, the current invention allows for a top-loading system rather than side loading. This is faster and easier for the surgeon. Further, the screw invention allows less torque to be placed on the screw in order to get the rod into the head which is potentially advantageous in terms of screw failure during manipulation to get the rod into rigid screws.

In the preceeding specification, all documents, acts, or information disclosed does not constitute an admission that the document, act, or information of any combination thereof was publicly available, known to the public, part of the general knowledge in the art, or was known to be relevant to solve any problem at the time of priority.

While there has been described and illustrated specific embodiments of an intervertebral spacer device, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described,

What is claimed is:
1. A surgical screw comprising:
   a bone anchor section;
   a screw body further comprising:
      a receiver body comprising:
         a cylindrical wall having a proximal edge and a distal edge;
         a spherical base disposed on the proximal edge of the cylindrical wall;
         a plurality of openings disposed in the cylindrical wall;
         an internal semi-circular, convex recess disposed in the spherical base for accepting the bone anchor section;
         an opening adjacent to the internal semi-circular, convex recess allowing the bone anchor section to project through the opening;

at least one rod saddle disposed within the receiver body adjacent to the spherical base and adapted to mate the receiver body with a rod, comprising:
two faces wherein a first mating face of the rod saddle is curved and adapted to mate with a rod and a second articulating face is curved and adapted to mate with the spherical base and allow articulation of the rod;
a compression nut, wherein the compression nut comprises a proximal face,
a distal face, and a receiver body interface wall adapted to interface with the receiver body;
wherein the distal face is conical; and
wherein the compression nut compresses the rod against the rod saddle.

2. The screw of claim 1, wherein the bone anchor further comprises:
a screw shaft;
anchor threads attached to the screw shaft and adapted for anchoring the bone screw to an anatomical body;
an anchor head attached to the screw shaft of the bone anchor section and adapted for connecting the bone screw to the receiver body.

3. The screw of claim 1, wherein at least one screw thread is disposed on the receiver body interface wall of the compression nut and is adapted to screw into the receiver using external threading.

4. The screw of claim 1, wherein the receiver body interface wall of the compression nut is adapted to snap into the receiver using external landings and grooves.

5. The screw of claim 2, wherein the anchor head, further comprises:
a narrow neck section disposed on a distal end of the screw shaft which expands into a convex mating section; and
a tool receiving indent disposed on a distal end of the convex mating section.

6. The screw of claim 5, wherein the tool receiving indent accepts a tool selected from the group consisting of hex driver, torx driver, Philips head screw driver, and flat head screw driver.

7. The screw of claim 2, wherein the anchor threads of the bone screw are selected from the group consisting of single leads, double leads, fixed screw leads, and variable screw leads.

8. The screw of claim 1, further comprising a rod locker disposed above the screw head within the receiver body, wherein the rod locker further comprises
a cylindrical wall having a proximal edge and a distal edge;
a base disposed on the proximal edge of the cylindrical wall adapted to mate with the receiver body;
an internal curved mating face disposed in the base adapted to accept the rod saddle; and
a plurality of openings disposed in the cylindrical wall adapted to receive the rod.

9. The screw of claim 8, wherein the plurality of openings disposed in the cylindrical wall are selected from the group consisting of spherical openings, U-shaped openings, and spherical U-shaped openings.

10. The screw of claim 1, wherein the plurality of openings disposed in the cylindrical wall of the receiver body are a plurality of U-shaped openings adapted to receive the rod.

11. The screw of claim 1, wherein the rod is selected from the group consisting of a cable, rod, bar, wire, and plate.

12. The screw of claim 1, wherein the rod saddle possesses at least one feature selected from the group consisting of concave mating face, convex mating face, and convex articulating face.

13. The screw of claim 12, wherein the rod saddle articulating face is a convex face selected from the group consisting of spherical, spheroidal, oval, and ovoid.

14. The screw of claim 1, wherein the rod saddle further comprises a locking mechanism disposed on at least one face of the rod saddle selected from the group consisting of: a rough surface, a notched surface, a knurled surface, and teeth.

15. The screw of claim 13, wherein the rod saddle is disposed below the rod, above the rod, or above and below the rod.

16. The screw of claim 8, further comprising an outer set nut adapted to compress the rod locker into receiver, comprising:
a proximal face and a distal face;
at least one wall disposed between the proximal and the distal face; and
a locking mechanism disposed on the at least one wall, wherein the locking mechanism is selected from the group consisting of threading and a plurality of landings and grooves.

17. A surgical screw comprising:
a bone anchor section further comprising:
a screw shaft having a proximal end and a distal end;
anchor threads attached to the screw shaft and adapted for anchoring the bone screw to an anatomical body;
an anchor head attached to the proximal end of the screw shaft of the bone anchor section and adapted for connecting the bone screw to a receiver body;
a screw body further comprising:
a receiver body comprising:
a cylindrical wall having a proximal edge and a distal edge;
a spherical base disposed on the proximal edge of the cylindrical wall adapted to accept an at least one rod saddle;
a plurality of openings disposed in the cylindrical walls;
an internal semi-circular, convex recess disposed in the spherical base adapted to mate with the anchor head;
an opening adjacent to the semi-circular, convex recess allowing the screw shaft and anchor threads of the bone screw to project through the opening;
a rod locker disposed above the screw head within the receiver body, wherein the rod locker further comprises;
a cylindrical wall having a proximal edge and a distal edge;
a base disposed on the proximal edge of the cylindrical wall adapted to mate with the receiver body;
an internal curved mating face disposed in the base adapted to accept an at least one rod saddle; and
a plurality of openings disposed in the cylindrical wall adapted to receive the rod;
at least one rod saddle disposed within the rod locker adjacent to the rod locker base and adapted to mate the receiver body with a rod, comprising two faces wherein a first mating face of the rod saddle is curved and adapted to mate with a rod and a second articulating face is curved and adapted to mate with the spherical base and allow articulation of the rod;
wherein the articulating face is a convex face selected from the group consisting of spherical, spheroidal, oval, and ovoid;
the rod disposed adjacent to the mating face of the rod saddle;

a compression nut, wherein the compression nut comprises a proximal face, a distal face, and a receiver body interface wall adapted to interface with the receiver body;

wherein the distal face is conical; and wherein the compression nut compresses the rod against the rod saddle.

18. The screw of claim 17, wherein the anchor head, further comprises:

a narrow neck section disposed on a distal end of the screw shaft which expands into a convex mating section; and a tool receiving indent disposed on a distal end of the convex mating section.

19. The screw of claim 18, wherein the tool receiving indent accepts a tool selected from the group consisting of hex driver, torx driver, Philips head screw driver, and flat head screw driver.

20. The screw of claim 17, wherein the compression nut is adapted to screw into the receiver using external threading.

21. The screw of claim 17, wherein the compression nut is adapted to snap into the receiver using external landings and grooves.

22. The screw of claim 17, wherein the anchor threads of the bone screw are selected from the group consisting of single leads, double leads, fixed screw leads, and variable screw leads.

23. The screw of claim 17, wherein the plurality of openings disposed in the cylindrical wall of the rod locker are selected from the group consisting of spherical openings, U-shaped openings, and spherical U-shaped openings.

24. The screw of claim 17, wherein the plurality of openings disposed in the cylindrical walls of the receiver body are a plurality of U-shaped openings adapted to receive the rod.

25. The screw of claim 17, wherein the rod is selected from the group consisting of a cable, rod, bar, wire, and plate.

26. The screw of claim 17, wherein the rod saddle further comprises a locking mechanism disposed on at least one face of the rod saddle selected from the group consisting of: a rough surface, a notched surface, a knurled surface, and teeth.

27. The screw of claim 17, further comprising an outer set nut adapted to compress the rod locker into receiver, comprising a proximal face and a distal face;

at least one wall disposed between the proximal and the distal face; and a locking mechanism disposed on the at least one wall, wherein the locking mechanism selected from the group consisting of threading and a plurality of landings and grooves.

* * * * *